United States Patent [19]
Rodriguez et al.

[11] 4,091,027
[45] May 23, 1978

[54] 6'-AMINO-SPIRO(CYCLOALKANE-1,2'-PENAM)-3'-CARBOXYLIC ACIDS

[75] Inventors: Ludovic Rodriguez, Brussels; Jacques Leclercq, Braine l'Alleud, both of Belgium

[73] Assignee: U C B Societe Anonyme, Brussels, Belgium

[21] Appl. No.: 800,082

[22] Filed: May 24, 1977

[30] Foreign Application Priority Data
May 25, 1976 United Kingdom ............... 21625/76

[51] Int. Cl.² ........................................... C07D 499/42
[52] U.S. Cl. .............................. 260/306.7 C; 424/270
[58] Field of Search ................ 260/239.1 TB, 306.7 C

[56] References Cited
U.S. PATENT DOCUMENTS

| | | | |
|---|---|---|---|
| 2,934,540 | 4/1960 | Sheehan | 260/306.7 C |
| 3,159,617 | 12/1964 | Sheehan | 260/306.7 C |

*Primary Examiner*—R. Gallagher
*Attorney, Agent, or Firm*—Wenderoth, Lind & Ponack

[57] ABSTRACT

6'-Amino-spiro[cycloalkane-1,2'-penam]-3'-carboxylic acids of the formula

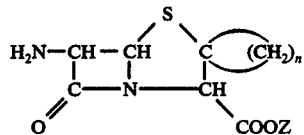

wherein Z is a hydrogen or an alkali metal atom, or a protective group, and $n$ a whole number of from 3 to 6, and process of preparing the same.

These compounds are useful as intermediates in the synthesis of a new group of antibiotics having properties similar to the penicillins.

6 Claims, No Drawings

6'-AMINO-SPIRO(CYCLOALKANE-1,2'-PENAM)-3'-CARBOXYLIC ACIDS

The present invention relates to new chemical compounds, namely, 6'-amino-spiro[cycloalkane-1,2'-penam]-3'-carboxylic acids and the salts and esters thereof, as well as to a process of preparing the same.

These new compounds are precursors of new penicillins, which are the subject matter of our Application Ser. No. 800,083 filed concurrently herewith. They also have a certain, although very slight, antibiotic activity.

The new compounds of the present invention have the general formula:

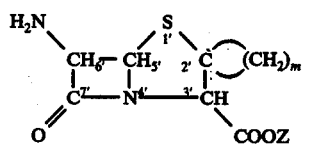
(I)

wherein Z is a hydrogen or an alkali metal atom or a group protecting the carboxylic function, for example a benzyl radical, and n is a whole number of from 3 to 6.

With regard to the stereochemistry of the new compounds, the existence of three asymmetric carbon atoms at $C_{3'}$, $C_{5'}$ and $C_{6'}$ should lead to the formation of 8 isomers which can be grouped into 4 racemic diastereoisomers. The kinetics of the reactions lead, in fact, to the formation of only 3 alpha-, beta- and gamma-racemates. The alpharacemate, the relative configurations of which correspond to those of penicillin, is preferably isolated from the mixture.

In the present specification and claims, the nomenclature used is that proposed by R. J. STOODLEY in Progress in Organic Chemistry, 8, (1973), 102–103. In particular, the name "penam" is given to the following ring system:

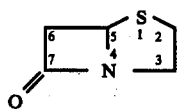

The compounds of general formula (I) of the present invention can be prepared by (1) reacting tert-butyl 2-formyl-2-phthalimido-acetate of the formula:

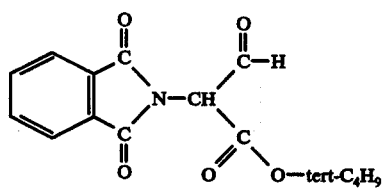
(II)

with an alpha-amino-1-mercapto-cycloalkaneacetic acid of the formula:

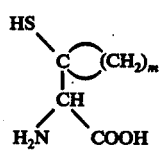
(III)

wherein n has the same meaning as above, to give the alpha-isomer of a tert-butyl alpha-phthalimido-thia-azaspiroalkaneacetate of the formula:

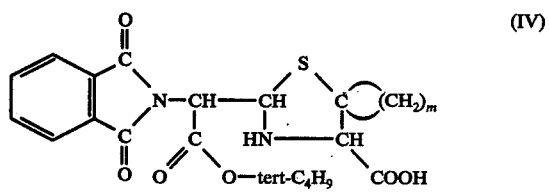
(IV)

wherein n has the same meaning as above;

(2) reacting the compound of formula IV with a benzyl halide to give a corresponding benzyl ester of the formula:

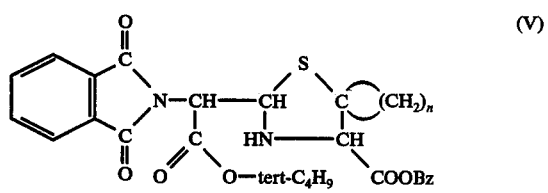
(V)

wherein n has the same meaning as above and Bz is a benzyl radical;

(3) subjecting the compound of formula V to hydrazinolysis to give a tert-butyl alpha-amino-thia-azaspiroalkaneacetate of the formula:

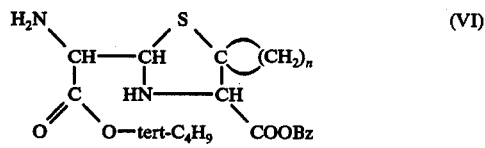
(VI)

wherein n and Bz have the same meanings as above;

(4) subjecting the compound of formula VI to partial acid hydrolysis to give a corresponding alpha-amino-thia-azaspiroalkaneacetic acid hydrochloride of the formula:

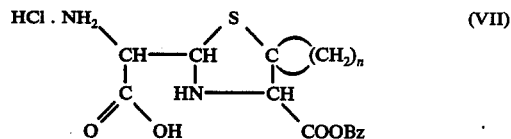
(VII)

wherein n and Bz have the same meanings as above;

(5) reacting the compound of formula VII with trityl chloride to give an alpha-tritylamino-thia-azaspiroalkaneacetic acid of the formula:

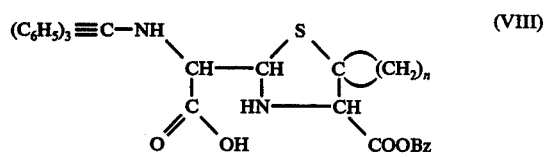
(VIII)

wherein n and Bz have the same meanings as above;

(6) cyclizing the compound of formula VIII with a carbodiimide to give a benzyl 6'-tritylamino-spiro[cycloalkane-1,2'-penam]-3'-carboxylate of the formula:

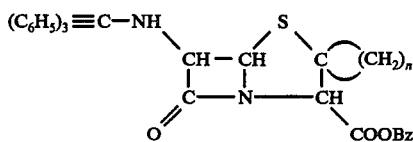

wherein n and Bz have the same meanings as above;

(7) treating the compound of formula IX with p-toluenesulfonic acid to give a benzyl 6'-amino-spiro[cycloalkane-1,2'-penam]-3'-carboxylate p-toluenesulfonate of the formula:

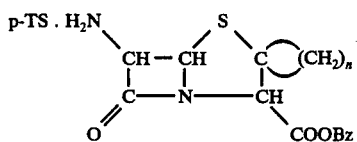

wherein p-TS represents p-toluenesulfonic acid and n and Bz have the same meanings as above; and (8) subjecting the compound of formula X to hydrogenolysis to give the 6'-amino-spiro[cycloalkane-1,2'-penam]-3'-carboxylic acid of the general formula (I) in which Z is a hydrogen atom.

The preparation of tert-butyl 2-formyl-2-phthalimido-acetate of formula II is described in literature (SHEEHAN et al., J. Am. Chem. Soc. 76, (1954), 158–160).

A method for the preparation of the alpha-amino-1-mercaptocycloalkaneacetic acids of formula III is, for example, as follows:

(1) An R' 2-isocyanoacetate of the formula:

C≡N—CH₂—COOR'     (XI)

wherein R' is an alkyl radical containing up to 3 carbon atoms or a benzyl radical, is condensed with a cycloalkanone of the formula:

wherein n has the same meaning as above, by means of a suspension of sodium hydride in tetrahydrofuran to give an R' 2-formamido-2-cycloalkylidene-acetate of the formula:

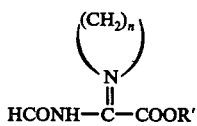

wherein n has the same meaning as above;

(2) which, by treatment with phosphorus pentasulfide (P₄S₁₀), is cyclized to give an R' thia-azaspiroalkanecarboxylate of the formula:

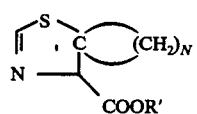

(3) the compound of formula XIV is then hydrolyzed, accompanied by decyclization, to give an alpha-amino-1-mercapto-cycloalkaneacetic acid of formula III.

It is obvious that in the case of compounds of formula III, it is possible to separate the two enantiomeric forms, thus leading directly to the desired pure diastereoisomer IV.

USES OF THE COMPOUNDS OF THE PRESENT INVENTION

The interest of the compounds of the present invention is that by simple reactions which are known per se, they lead to new groups of compounds similar to the penicillins. These compounds, which have the general formula:

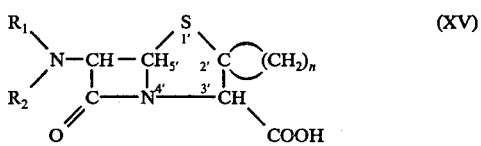

as well as processes for preparing the same and uses thereof, are the subject matter of our Application Ser. No. 800,083 filed concurrently herewith, to which reference is made for a detailed description.

The substituents —NR₁R₂ are the conventional substituents known from the chemistry of penicillins, such as those mentioned, for example, in Ullmann's Encyklopaedie der Technischen Chemie, 4th edition, vol. 7, (1974), pages 651 and 652.

By way of example, from the new compounds of the present invention, it is possible to obtain acids of formula XV, in which n is a whole number of from 3 to 6, R₁ is a hydrogen atom and R₂ is a 2-phenylacetyl, 2,6-dimethoxybenzoyl, 2-amino-2-phenylacetyl, 5-methyl-3-phenyl-4-isoxazolecarbonyl or 2-carboxy-2-phenylacetyl radical, or R₁ and R₂ together represent a bivalent radical, for example a (hexahydro-1H-azepin-1-yl) methylene radical and the pharmaceutically acceptable, non-toxic salts thereof.

These compounds differ from known penicillins solely with respect to the presence of the polymethylene chain in the 2'-position.

The compounds of formula XV, in which R₁ is a hydrogen atom and R₂ is a radical known from the chemistry of penicillins, for example one of the above-mentioned radicals, can be obtained by subjecting the new compounds of the present invention to an acylation reaction using a halide of an organic monocarboxylic acid of the general formula R₂OH or a functional equivalent thereof, R₂ having the same meaning as above. Thus, for example, it is possible to use phenylacetyl chloride, 2,6-dimethoxy-benzoyl chloride, 5-methyl-3-phenyl-4-isoxazolecarbonyl chloride, 2-phenyl glycyl chloride or 2-carboxy-2-phenylacetyl chloride as acylating agent.

The functional equivalents of the above-mentioned acid halides which can be used as acylating agents for the primary amino radical of the 6'-amino-spiro[cycloalkane-1,2'-penam]-3'-carboxylic acids are, in particular, the acid anhydrides, including mixed anhydrides and especially the mixed anhydrides formed with stronger acids, such as the lower aliphatic monoesters of carbonic acid, the alkylsulfonic and arylsulfonic acids and acids having a more pronounced hindrance, such as diphenylacetic acid. In addition, an acid azide or an active ester or thioester (for example with p-nitrophenol, 2,4-dinitrophenol, thiophenol or thioacetic acid) may be used but, as an alternative, the free acid itself may be condensed with the 6'-aminospiro[cycloalkane-1,2'-penam]-3'-carboxylic acid after the free acid has previously been activated by reaction with (chloromethylene)dimethylammonium chloride (see British Pat. Specification No. 1,008,170 and Novak and Weichet, Experientia, XXI, 6, (1965), 360) or by means of enzymes, or with an N,N'-carbonyldiimidazole or an N,N'-carbonylditriazole (see British Pat. Specification No. 967,108) or with a carbodiimide, for example N,N'-dicyclohexylcarbodiimide, N,N'-diisopropylcarbodiimide or N-cyclohexyl-N'-(2-morpholinoethyl)-carbodiimide (see Sheehan and Hess, J. Am. Chem. Soc. 77, (1955), 1067) or an alkynylamine (see Buijle and Viehe, Angew. Chem., International Edition, 3, (1964), 582) or a ketene-imine (see Stevens and Munk, J. Am. Chem. Soc. 80, (1958), 4065) or an isoxazolium salt (see Woodward et al., J. Am. Chem. Soc. 83, (1961), 1010). Instead of the acid halides, the corresponding azolides can also be used.

When the starting compound used is an ester of the 6'-amino-spiro[cycloalkane-1,2'-penam]-3'-carboxylic acid, generally the benzyl ester, the process includes a second stage which comprises hydrogenolyzing the esters obtained to the corresponding acids.

The starting compounds may be, as desired, 6'-amino-spiro[cycloalkane-1,2'-penam]-3'-carboxylic acids, or the salts or esters thereof. Nevertheless, we have found that, with regard to the yield, it is preferable to start with esters in certain cases and with the acids themselves in other cases. Particularly when the substituent $R_2$ is a 2-phenylacetyl, 2,6-dimethoxy-benzoyl or 2-amino-2-phenylacetyl radical, it is preferable to start with an ester, for example the benzyl ester, of the corresponding 6'-amino-spiro[cycloalkane-1,2'-penam]-3'-carboxylic acid and to subject the resulting compound to a subsequent debenzylation reaction in order to obtain the free acid. When, on the other hand, the substituent $R_2$ is a 5-methyl-3-phenyl-4-isoxazolecarbonyl or 2-carboxy-2-phenylacetyl radical, it is then preferable to start with the acid itself. Nevertheless, it must not be overlooked that the 6'-amino-spiro[cycloalkane-1,2'-penam]-3'-carboxylic acids are themselves always obtained from the corresponding esters because it is necessary to protect the acid group temporarily. In other words, the stage of conversion of the ester into acid is not an additional stage, because it is, in fact, simply shifted in the general synthesis process: in some cases, it is effected before the acylation reaction and in other cases after the acylation reaction.

Similarly, we have also found that there is a relationship between the nature of the substituent in the 2'-position and the ease of effecting the acylation of the ester and then the deprotection or of first effecting the deprotection and only then the acylation of the acid. Thus, when $R_2$ is a 2-amino-2-phenylacetyl radical, it is preferable to effect the acylation on the acid when $n$ is 5, whereas it is preferable to effect it on the ester when $n$ is 4.

By "pharmaceutically acceptable, non-toxic salts" are to be understood, in particular, the salts of metals, such as sodium, potassium, calcium and aluminium, ammonium salts and the salts of amines, such as trialkylamines, particularly triethylamine, procaine, dibenzylamine, N-benzyl-beta-phenethylamine, L-ephenamine, N,N'-dibenzyl-ethylenediamine, dehydroabietylamine, N,N'-bis-dehydroabietylethylenediamine, the N-(lower alkyl)-piperidines, such as N-ethylpiperidine, and, more generally, the salts already known for penicillins G and V (see Ullmann's Encyklopaedie, loc. cit., p. 653). These salts can be obtained from the corresponding acids by known methods.

When the radical $R_2$ is, for example, a 2-amino-2-phenylacetyl radical, the compounds may also be in the form of addition salts with pharmaceutically acceptable acids, for example acetic, citric, succinic, ascorbic, hydrochloric, hydrobromic, sulfuric and phosphoric acids.

The compounds of formula XV, in which $R_1$ and $R_2$ represent together a bivalent radical $R_3$, can be obtained from the compounds of the present invention by reaction with an activated derivative of a compound of the formula $R_3=O$. Thus, for example, when the radical $R_3$ is a (hexahydro-1H-azepin-1-yl)methylene radical, 6'-amino-spiro-[cycloalkane-1,2'-penam]-3'-carboxylic acid or a salt or an ester thereof is reacted with an activated derivative of hexahydro-1H-azepin-1-carboxaldehyde. The activated derivatives of compounds $R_3=O$ are generally the corresponding amide chlorides obtained by the reaction with oxalyl chloride or the complex obtained by the reaction with dimethyl sulfate.

The compounds of formula XV and also their pharmaceutically acceptable, non-toxic salts are used as antibacterial agents, as dietetic supplements for animal foodstuffs and as therapeutic agents for man and animals in the treatment of infectious diseases caused by Gram-positive and Gram-negative bacteria, these compounds having a very broad spectrum of antibacterial activity against both Gram-positive and Gram-negative bacteria.

ANTIBACTERIAL ACTIVITY

Numerous comparative tests have been carried out in respect of the biological activity of some compounds obtained from the compounds of the present invention towards various bacterial strains of the Gram-positive and Gram-negative type. The reference compounds for the comparative tests are penicillin G, oxacillin, methicillin, ampicillin and penicillanic acid. Some information regarding the origins and characteristics of the bacterial strains used are first given below.

A. GRAM-POSITIVE BACTERIAL STRAINS

SARCINA LUTEA

This is a Gram-positive coccus which is very sensitive to penicillins. It is a typical example of a bacterium having no resistance mechanism towards penicillins and a model of an unprotected bacterial receptor. Consequently, the antibacterial activity upon this strain could be likened to a measure of the activity on a receptor.

STAPHYLOCOCCUS AUREUS 6538

This is also a Gram-positive coccus which is particularly sensitive to penicillins and which has a poor resistance mechanism. This strain of Staphylococcus is, therefore, representative of a maximum sensitivity of the species.

STAPHYLOCOCCUS AUREUS 52149.

This is a Gram-positive coccus, for which the intrinsic sensitivity of the receptor is equivalent to that of the preceding strain but which produces a beta-lactamase typical of the species, which makes it resistant to all penicillins sensitive to hydrolysis.

B. GRAM-NEGATIVE BACTERIAL STRAINS

ESCHERICHIA COLI B

This is a classical collection strain of *Escherichia coli* which produces very little beta-lactamase (of type I) and is, therefore, very sensitive to penicillins. With regard to the classification of the beta-lactamases, use is here made of that proposed by M. H. Richmond and R. B. Sykes in Advances in Microbial Physiology, 9, (1973), pages 43 and 45.

ESCHERICHIA COLI B-AMPI R

This is a mutant of the preceding strain which we have produced. This strain, on the other hand, is a hyperproducer of beta-lactamase of type I already produced by the parent strain Escherichia Coli B. It has an increased resistance to penicillins, which appears to be directly connected with the production of beta-lactamase.

ESCHERICHIA COLI K 12-44

This is a mutant of *Escherichia coli* K 12, the typical reference parent strain of the species. This mutant does not produce beta-lactamase.

ESCHERICHIA COLI K 12-44-TEM

This strain is obtained from a strain of *Escherichia coli* K 12-44 in which the episome TEM, which is, in particular, responsible for the production of a beta-lactamase of type III, has been transferred.

ESCHERICHIA COLI K 12-44 S

This is a pleiotropic mutant of *Escherichia coli* K 12-44, which does not produce beta-lactamase and which is a strain which we have produced. It is very sensitive to penicillins due to hyperpermeability.

C. RESULTS OF COMPARATIVE ACTIVITY TESTS

The minimum inhibiting concentration (abbreviated as MIC) has been determined for a certain number of compounds by the procedure described below.

The products are introduced in increasing concentration into a gelose culture medium in Petri dishes. A multiple inoculator is used for simultaneously depositing drops (i.e. a total of 10 microliters) of inoculum (suspension containing about $10^5$ bacteria per ml.) on the surface of the medium. After incubation at 37° C., for 24 hours, the growth of the bacteria is observed. By definition, the MIC is expressed (in micromoles) by the minimum concentration inhibiting the multiplication of the bacteria.

In all the results given below, the MIC is taken as being equal to 1 for the reference products and the activity figures indicated for the compounds tested are, therefore, relative values. This presentation of the results is the most correct and the most reproducible because, for the same bacterial strain, it is possible to observe different values of MIC if they are measured at different times. This is connected with "seasonal" variations of the strains and of their nutrient medium. Nevertheless, by way of indication, the absolute value of the MIC for the reference compounds, expressed in micromoles, is, in each case, also indicated in brackets.

a) Comparative tests with penicillin G.

| Strain used | penicillin G | Compound A | Compound B | Compound C |
|---|---|---|---|---|
| SARCINA LUTEA | 1 (0.01) | 1.6 | — | 2 |
| S.AUREUS 6538 | 1 (0.125) | 2.5 | 0.5 | 1 |
| E.COLI B | 1 (16) | 11 | 3.4 | 4 |
| S.AUREUS 52149 | 1 (3.1) | — | — | 1 |

Compound A: potassium 6'-(2"-phenylacetamido)-spiro[cyclohexane-1,2'-penam]-3'-carboxylate.
Compound B: potassium 6'-(2"-phenylacetamido)-spiro[cyclopentane-1,2'-penam]-3'-carboxylate.
Compound C: potassium 6'-(2"-phenylacetamido)-spiro[cyclobutane-1,2'-penam]-3'-carboxylate.

b) Comparative tests with oxacillin.

| Strain used | oxacillin | Compound D |
|---|---|---|
| S.AUREUS 6538 | 1 (1.25) | 1-0.65 |
| S.AUREUS 52149 | 1 (1.25) | 0.55 |

Compound D: sodium 6'-(5"-methyl-3"-phenyl-4"-isoxazole-carboxamide)-spiro[cyclohexane-1,2'-penam]-3'-carboxylate.

Comparative tests with methicillin.

| Strain used | methicillin | Compound E | Compound F |
|---|---|---|---|
| S.AUREUS 6538 | 1 (3.1) | 1.25 | 0.4 |
| S.AUREUS 52149 | 1 (6.25) | 0.55 | 0.4 |

Compound E: sodium 6'-(2",6"-dimethoxybenzamido)-spiro]cyclohexane-1,2'-penam]-3'-carboxylate.
Compound F: sodium 6'-(2",6"-dimethoxybenzamido)-spiro[cyclopentane-1,2'-penam]-3'-carboxylate.

d) Comparative tests with ampicillin.

| Strain used | ampicillin | Compound G | Compound H |
|---|---|---|---|
| S.AUREUS 6538 | 1 (0.08-0.2) | 1 | 1 |
| E.COLI B | 1 (1.3) | 30 | 3.8 |
| E.COLI B AMPI-R | 1 (27.5-56) | >2 | 2 |
| E.COLI K 12-44 | 1 (4.5-4.9) | 10 | 4.2 |
| E.COLI K 12-44 TEM | 1 | 1 | 1 |
| E.COLI K 12-44 S | 1 (1.25) | — | 2.6 |

Compound G: sodium 6'-(2"-amino-2"'-phenylacetamido)-spiro[cyclohexane-1,2'-penam]-3'-carboxylate.
Compound H: 6'-(2"-amino-2"'-phenylacetamido)-spiro[cyclopentane-1,2'-penam]-3'-carboxylic acid.

e) Comparative tests with penicillanic acid.

| Strain used | penicillanic acid | Compound I |
|---|---|---|
| SARCINA LUTEA | 1 (55) | 0.32 |
| S.AUREUS 6538 | 1 (165) | 0.5 |
| E.COLI B | 1 (30) | 2 |
| E.COLI B AMPI-R | 1 (70) | >2 |

Compound I: 6'-amino-spiro[cyclohexane-1,2'-penam]-3'-carboxylic acid.

This compound is one of the compounds of the present invention and these results show that its antibacterial activity exists, even if it remains very slight.

D. POSOLOGY AND FIELDS OF USE

The compounds of the present invention can be administered orally or parenterally.

The limits indicated hereinbelow are only approximate because they are essentially deduced from the MIC values. For the values in vivo, other factors are involved, for example blood level, resorption, metabolization and elimination, the influence of which can be determined only by clinical experience. This has the practical consequence that, with an equal MIC value, two compounds may, nevertheless, have a different posology.

A. HOMOLOGUES OF PENICILLIN G

Penicillin G is used in the treatment of infections caused by non-resistant Gram-positive bacteria. Posology is between 0.2 and 3.0 g. per day.

Compound A, for the same application, can be used in doses between about 0.5 and 7.0 g. per day.

Similarly, compound B can be used in doses between 0.1 and 1.5 g. per day, and compound C between 0.2 and 3.0 g. per day.

B. HOMOLOGUES OF OXACILLIN

Oxacillin is used in the treatment of infections due to penicillin-resistant Staphylococci producing beta-lactamase. The posology is between 4 and 8 g. per day.

For the same use, compound D can be used in doses between 2 and 4 g. per day.

C. HOMOLOGUES OF METHICILLIN

In the same field of use as oxacillin, the posology is about 2 g. per day.

For the same use, compound E may be administered in doses ranging from 1 to 2 g. per day, compound F in a dose of about 1 g. per day.

D. HOMOLOGUES OF AMPICILLIN

Ampicillin is used in the treatment of infections caused by a very broad spectrum of bacteria which covers not only Gram-positive but also Gram-negative bacteria. The posology is between 0.2 and 2 g. per day.

Compound G, which acts essentially on Gram-positive bacteria, can be used in doses between 0.5 and 1 g. per day. It also has activity against Gram-negative bacteria but in doses which therapeutically are too high.

On the other hand, compound H behaves more closely to ampicillin, with a posology of 0.5 to 2 g. per day for Gram-positive bacteria and a posology of from 2 to 8 g. for Gram-negative bacteria.

E. HOMOLOGUES OF 6-AMINO-PENICILLANIC ACID

These products are not used therapeutically. However, solely by way of indication, the activity spectra of penicillanic acid has been compared with that of compound I. This shows that compound I has a better activity than 6-amino-penicillanic acid for Gram-positive bacteria and a lower activity for Gram-negative bacteria.

The following Examples are given for the purpose of illustrating the present invention. For greater clarity and better understanding, we have grouped together certain synthesis stages.

I. PREPARATION OF ALPHA-AMINO-1-MERCAPTO-CYCLOALKANEACETIC ACIDS

1. Alpha-amino-1-mercapto-cyclobutaneacetic acid (III; $n=3$)

a. Ethyl 2-formamido-2-cyclobutylidene-acetate (XIII; $n=3$) 2.24 g. of 50% sodium hydride (0.04 mole) are introduced into a round-bottomed flask, provided with a magnetic stirrer, in an inert atmosphere (for example nitrogen) and washed twice with 30 ml. amounts of dry benzene and then twice with 30 ml. amounts of dry tetrahydrofuran. Then, 50 ml. dry tetrahydrofuran are added. A solution of 4.52 g. (0.04 mole) of ethyl 2-isocyanoacetate and 2.80 g. (0.04 mole) of cyclobutanone in 50 ml. of dry tetrahydrofuran is then added dropwise to this suspension of sodium hydride. The temperature of the reaction mixture is 35° C. and hydrogen is evolved. Stirring is continued for 12 hours at ambient temperature. The solvent is then evaporated and the residual oil is taken up in 100 ml. of water containing 2.40 g. (0.04 mole) of glacial acetic acid. The product is extracted four times with 70 ml. amounts of diethyl ether, the ethereal phase is dried and the ether evaporated off. 4.30 g. of ethyl 2-formamido-2-cyclobutylidene-acetate are obtained in the form of an oil which is sufficiently pure for direct use in the subsequent reaction. The yield is 57.5%.

| NMR spectrum (in CDCl$_3$-tetramethylsilane (TMS)): | | |
|---|---|---|
| 1.3 ppm | triplet | 3H (—CH$_3$) |
| 1.7 to 2.4 ppm | multiplet | 2H (—CH$_2$—cyclobutyl) |
| 2.6 to 3.4 ppm | multiplet | 4H (2 × —CH$_2$—cyclobutyl) |
| 4.25 ppm | quartet | 2H (—O—CH$_2$—) |
| 7.3 to 8.0 ppm | multiplet | 1H (NH) |
| 8.2 ppm | singlet | 1H (H—C$\overset{O}{\underset{}{\diagup}}$) | b. Ethyl 5-thia-7-azaspiro[3.4]oct-6-ene-8-carboxylate (XIV; $n=3$) 1.3 g. (0.0058 mole) of phosphorus pentasulfide (P$_4$S$_{10}$) is added to a suspension of 4.3 g. (0.023 mole) of ethyl 2-formamido-2-cyclobutylidene-acetate in 50 ml. of dry benzene in a round-bottomed flask, while stirring with a magnetic stirrer. The reaction mixture is heated under reflux for 4 hours. The benzene phase is then decanted, the benzene evaporated off and the residue is distilled (140° C./0.005 mm.Hg.). 1.0 g. of an oil is obtained which is identified as being ethyl 5-thia-7-azaspiro-[3.4]-oct-6-ene-8-carboxylate.

| NMR spectrum (in CDCl$_3$-TMS): | | |
|---|---|---|
| 1.35 ppm | triplet | 3H (CH$_3$) |
| 1.6 to 2.9 ppm | multiplet | 6H (3 × CH$_2$ cyclobutyl) |
| 4.33 ppm | quartet | 2H (—O—CH$_2$—) |
| 4.9 ppm | doublet | 1H (H$_8$) |
| 8.17 ppm | doublet | 1H (H$_6$) |
| I.R. spectrum (film) | 2870,2935 and 2975 cm$^{-1}$ | (—CH$_2$—cyclobutyl) |
| | 1728 cm$^{-1}$ | (C=O ester) |
| | 1565 cm$^{-1}$ | (C=N) | c. Alpha-amino-1-mercapto-cyclobutaneacetic acid. 1 g. of ethyl 5-thia-7-azaspiro[3.4]oct-6-ene-8-carboxylate and 50 ml. 6N hydrochloric acid are introduced into a round-bottomed flask, with magnetic stirring. The reaction mixture is heated under reflux for 4 hours. It is then evaporated to dryness and the residue is washed with diethyl ether and recrystallized from acetone. 1.0 g. of alpha-amino-1-mercapto-cyclobutaneacetic acid is thus obtained in the form of its hydrochloride. Yield: 88.7%.

| NMR spectrum (in dimethyl sulfoxide (DMSO-TMS) : | | |
|---|---|---|
| 1.6 to 2.4 ppm and 2.4 to 2.9 ppm | multiplet | 6H (3 × CH$_2$ cyclobutyl) |
| 4.32 ppm | singlet | 1H (H alpha to —COOH) |
| 8 to 9 ppm (in D$_2$O): | multiplet | ± 4H (—NH$_3^+$, —COOH) |
| 1.5 to 3.3 ppm | multiplet | 6H (3 × CH$_2$ cyclobutyl) |
| 4.45 ppm | singlet | 1H (H alpha to —COOH) |

Analysis: C$_6$H$_{11}$NO$_2$S.HCl calculated: C 36.64%; H 6.10%; N 7.12%. found: C 36.50%; H 6.09%; N 7.13%.

I.R. spectrum (KBr): 3250 cm$^{-1}$ (NH); 1740 cm$^{-1}$ (COOH).

2. Alpha-amino-1-mercapto-cyclohexaneacetic acid (III; n=5)

a. Ethyl 2-formamido-2-cyclohexylidene-acetate (XIII; n=5). 90.4 g. (0.8 mole) of ethyl 2-isocyanoacetate and 78.0 g. (0.8 mole) of cyclohexanone, dissolved in 600 ml. of anhydrous tetrahydrofuran, are added to a suspension of 20 g. of sodium hydride in 1 liter of dry tetrahydrofuran in a round-bottomed flask provided with a magnetic stirrer, in an inert atmosphere, for example nitrogen. The addition time is about one hour and the temperature of the reaction mixture is kept at about 25° C. by means of an ice-bath. Stirring is then continued for 3 hours at ambient temperature, whereupon the solvent is evaporated off under reduced pressure. The residue is taken up in 1 liter of water containing 72 g. of glacial acetic acid and then extracted with diethyl ether (once with 1.5 liter and twice with 1 liter). The ethereal phases are combined and dried and the diethyl ether is evaporated off. 150 g. of crude product is obtained which is filtered through silica (eluent: chloroform) so as to obtain finally, after trituration with hexane, 104 g. of ethyl 2-formamido-2-cyclohexylidene acetate (yield 61.8%; M.P. 86° C. Analysis: $C_{11}H_{17}NO_3$ calculated: C 62.56%; H 8.06%; N 6.64%. found: C 61.89%; H 8.28%; N 6.57%.

I.R. spectrum (KBr): 3290 $cm^{-1}$ (NH); 1720 $cm^{-1}$ (CO ester); 1660 $cm^{-1}$ (CO amide).

| NMR spectrum (in $CDCl_3$-TMS): | | |
|---|---|---|
| 1.3 ppm | triplet | 3H (J=6.5 cycles per second) ($CH_3$ of ethyl ester) |
| 1.65 ppm | multiplet | 6H (—($CH_2$)$_3$— of cyclohexyl) |
| 2.30 ppm | multiplet | 2H (—$CH_2$— alpha to the double bond) |
| 2.75 ppm | multiplet | 2H (—$CH_2$— alpha to the double bond) |
| 4.25 ppm | quartet | 2H (—$CH_2$— of ethyl ester) |
| 6.10 ppm | multiplet | 1H (—NH—) |
| 8.25 ppm | singlet | 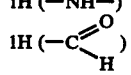 | b. Ethyl 1-thia-3-azaspiro[4.5]dec-2-ene-4-carboxylate (XIV; n=5) 21.8 g. (0.1 mole) of phosphorus pentasulfide ($P_4S_{10}$ form) is added to a solution of 75 g. of ethyl 2-formamido-2-cyclohexylidene-acetate in 450 ml. of dry benzene, in a round-bottomed flask, while stirring with a magnetic stirrer. The reaction mixture is heated under reflux for 4 hours. The benzene phase is then decanted, the benzene evaporated off and the residue is distilled (120° C./0.05 mm.Hg.). 21 g. ethyl 1-thia-3-azaspiro[4.5]dec-2-ene-4-carboxylate are obtained. Yield: 92.5%.

| NMR spectrum ($CDCl_3$-TMS): | | |
|---|---|---|
| 1.30 ppm | triplet | 3H (J=6.5 cycles per second) ($CH_3$ of ethyl ester) |
| 1.75 ppm | multiplet | 10H (—($CH_2$)$_5$—cyclohexyl) |
| 4.30 ppm | quartet | 2H (J=6.5 cycles per second) (—$CH_2$— ester) |
| 4.61 ppm | doublet | 1H (J=2.5 cycles per second) ($H_4$) |
| 8.15 ppm | doublet | 1H (J=2.5 cycles per second) ($H_2$) | c. Alpha-amino-1-mercapto-cyclohexaneacetic acid. This compound is obtained from ethyl 1-thia-3-azaspiro[4.5]-dec-2-ene-4-carboxylate by the process described in 1c) above.

Analysis: $C_8H_{15}NO_2S\cdot HCl$ calculated: C 42.57%; H 7.10%; N 6.25%. found: C 40.20%; H 7.37%; N 5.66%.

| NMR spectrum (in DMSO - sodium dimethyl-2,2-sila-2-pentanesulfonate (DSS)): | | |
|---|---|---|
| 1.7 ppm | multiplet | 10H (—($CH_2$)$_5$—cyclohexyl) |
| 4.02 ppm | singlet | 1H (H alpha to COOH) |
| 8 to 9 ppm | multiplet | 4H (—$NH_3^+$, COOH) |

3. Alpha-amino-1-mercapto-cycloheptaneacetic acid (III; n=6)

a. Ethyl 2-formamido-2-cycloheptylidene-acetate (XIII; n=6) A suspension of 0.1 mole of sodium hydride in 100 ml. of dry tetrahydrofuran is introduced into a round-bottomed flask provided with a magnetic stirrer in a dry inert atmosphere (for example nitrogen). During the course of one hour, a solution of 11.2 g. (0.1 mole) of cycloheptanone and 11.3 g. (0.1 mole) of ethyl 2-isocyanoacetate in 60 ml. of dry tetrahydrofuran are added dropwise to this suspension. Stirring is continued for 3 hours further at ambient temperature. The solvent is then evaporated off and the residue is taken up in 100 ml. of water containing 9.5 g. glacial acetic acid. The product is extracted several times with diethyl ether, the ethereal phase is dried and the diethyl ether is evaporated. 20 g. of crude product are obtained and partially purified on a silica column (eluent: ethyl acetate) to give 15.5 g. of product which is recrystallized from a mixture of ethanol and hexane. There are thus obtained 10.0 g. (yield 44.4%) of ethyl 2-formamido-2-cycloheptylidene-acetate. M.P. 69° C.

Analysis: $C_{12}H_{19}NO_3$ calculated: C 64.00%; H 8.44%; N 6.22%. found: C 63.12%; H 8.64%; N 6.67%.

| NMR spectrum ($CDCl_3$—TMS): | | |
|---|---|---|
| 1.3 ppm | triplet | 3H (J=7 cycles per second) ($CH_3$ ester) |
| 1.6 ppm | singlet | 8H (—($CH_2$)$_4$—cycloheptyl) |
| 2.5 ppm<br>2.8 ppm | 2 singlets (broad) | 4H (—$CH_2$—alpha to the double bond) |
| 4.27 ppm | quartet | 2H (—$CH_2$—ester) |
| 7.1 ppm | multiplet | 1H (—NH—) |
| 8.25 ppm | singlet | 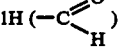 |

I.R. spectrum (KBr): 3250 $cm^{-1}$ (NH); 1725 $cm^{-1}$ (CO ester); 1650 $cm^{-1}$ (CO amide).

b. Ethyl 1-thia-3-azaspiro[4.6]undec-2-ene-4-carboxylate (XIV; n=6) 2.7 g. (0.012 mole) of phosphorus pentasulfide ($P_4S_{10}$ form) are added to a suspension of 10 g. (0.0445 mole) of ethyl 2-formamido-2-cycloheptylidene-acetate in 70 ml. of dry benzene in a round-bottomed flask, with mechanical stirring. The mixture is heated under reflux for 5 hours, then filtered through Norit, the benzene is evaporated in vacuo and the residue is distilled (130° C./0.2 mm.Hg.). There are obtained 2.9 g. (yield 27.5%) of ethyl 1-thia-3-azaspiro[4.6]undec-2-ene-4-carboxylate, with a purity of 80% (determined by gas phase chromatography).

| NMR spectrum (in $CDCl_3$-TMS): | | |
|---|---|---|
| 1.3 ppm | 2 triplets | 3H (—$CH_3$ ester) |
| 1.6 ppm | broad singlet | ± 12H (—($CH_2$)$_6$—cycloheptyl) |
| 4.2 ppm | superimposed quartets | 2H (—$CH_2$—ester) |
| 4.6 ppm | 2 singlets | 1H ($H_4$) |
| 8.2 ppm | 2 singlets | 1H ($H_2$) | c. Alpha-amino-1-mercapto-cycloheptaneacetic acid.

2.8 g. (0.012 mole) of ethyl 1-thia-3-azaspiro[4.6]undec-2-ene-4-carboxylate and 70 ml. of 6N hydrochloric acid are heated under reflux for 10 hours in a round-bottomed flask, while stirring. The reaction mixture is then evaporated to dryness and the residue is taken up in a mixture of 100 ml of dry benzene and 100 ml. of absolute ethanol. The reaction mixture is evaporated to dryness, taken up twice again in 100 ml. of dry benzene and evaporated to dryness to eliminate the last traces of water. 24 g. of crude alpha-amino-1-mercapto-cycloheptaneacetic acid, which is sufficiently pure for subsequent reaction, are thus obtained. A sample is recrystallized from a mixture of acetonitrile and diethyl ether. M.P. 120°–125° C. (decomposition). The purified product gives a single spot by thin-layer silica chromatography (eluent: n-butanol-pyridine-water; 6:2:2).

| NMR spectrum (in DMSO-TMS): | | |
|---|---|---|
| 1.5 ppm | multiplet | 12H (—(CH$_2$)$_6$—cycloheptyl) |
| 3.5 ppm | singlet | 1H (SH) |
| 3.95 ppm | singlet | 1H (H alpha to COOH) |

I.R. spectrum (KBr): 3400 cm$^{-1}$ (NH); 2940 cm$^{-1}$ (—CH$_2$—); 2520 cm$^{-1}$ (SH); 1715 cm$^{-1}$ (COOH); 1570 and 1595 cm$^{-1}$ (NH$_3{}^+$); from 3100 to 2000 cm$^{-1}$ (hydrochloride).

4. Alpha-amino-1-mercapto-cyclopentaneacetic acid (III; $n=4$)

This compound is prepared in the same manner as the three compounds previously described. M.P. 199° C.

Analysis: C$_7$H$_{13}$NO$_2$S.HCl calculated: C 39.9%; H 6.15%; N 6.60%. found: C 38.0%; H 6.38%; N 7.01%.

| NMR spectrum (in DMSO-TMS): | | |
|---|---|---|
| 1.9 ppm | singlet | 8H (—(CH$_2$)$_4$—cyclopentyl) |
| 4.08 ppm | singlet | 1H (H alpha to COOH) |
| 9.2 ppm | multiplet | ± 4H (NH$_3{}^+$, COOH, SH) |

II. PREPARATION OF TERT-BUTYL ALPHA-PHTHALIMIDO-THIA-AZASPIROALKANEACETATES AND THE CORRESPONDING BENZYL ESTERS

1.1. Tert-butyl 4-carboxy-alpha-phthalimido-1-thia-3-azaspiro[4.5]decane-2-acetate (IV; $n=5$).

144.4 g. (0.5 mole) of tert-butyl 2-formyl-2-phthalimido-acetate 113 g. (0.5 mole) of alpha-amino-1-mercapto-cyclohexane-acetic acid hydrochloride, 62 g. (0.75 mole) of sodium acetate, 1.7 liter of ethanol and 1.7 liter of water are mixed in a round-bottomed flask at ambient temperature. The suspension is progressively heated until dissolution is complete (at about 65° C.). It is then allowed to cool in an atmosphere of nitrogen and stirred for 20 hours at ambient temperature. A precipitate is obtained which is filtered off (retaining the filtrate), washed with water and redissolved in chloroform. The resulting solution is dried over anhydrous sodium sulfate and, after evaporation to dryness, 173 g. of residue are obtained. The above-mentioned filtrate is evaporated in vacuo to eliminate the ethanol and the water and, by extraction with chloroform and subsequent evaporation, 108 g. of a viscous oil are obtained.

The two extracts are combined and epimerized in pyridine, using the following method:

To a given amount of the mixture of diastereoisomers there is added 1.5 times its weight of anhydrous pyridine. This solution is heated overnight at 100° C. in an atmosphere of nitrogen and with gentle stirring. It is then placed in a refrigerator at −5° C. after being seeded with crystals of the desired alpha diastereoisomer, previously obtained after seven fractional recrystallizations of an aliquot of the mixture of diastereoisomers obtained. The resulting precipitate is filtered off and washed with a mixture of hexane and acetone (80/20) to give the pure alpha isomer. The mother liquors are concentrated in vacuo, weighed and again subjected to the above treatment until no further precipitate is obtained. Yield: 47%. M.P. 214°–215° C. (decomposition).

Analysis: C$_{23}$H$_{28}$N$_2$O$_6$S calculated: C 60.0%; H 6.08%; N 6.08%. found: C 59.9%; H 6.11%; N 6.03%.

| NMR spectrum (in DMSO-DSS): | | |
|---|---|---|
| 1.42 ppm | singlet | 9H (tert-butyl) |
| 1.62 ppm | multiplet | 10H (cyclohexyl) |
| 3.50 ppm | singlet | 1H (H$_4$) |
| 4.90 ppm | quartet | 2H (H$_2$ and H alpha to ester) |
| 8.0 ppm | singlet | 4H (aromatic) |

I.R. spectrum: 3325 cm$^{-1}$ (NH); 1755 cm$^{-1}$ (CO of the phthalimido group); 1735 cm$^{-1}$ (CO of the ester); 1710 cm$^{-1}$ (CO of the acid). 758 cm$^{-1}$ (ortho-disubstituted phenyl)

Mass spectrum: M$^{+\cdot}$ at m/e 460

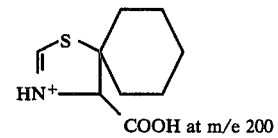

COOH at m/e 200

1.2. Tert-butyl 4-carboxy-alpha-phthalimido-1-thia-3-azaspiro[4.4]nonane-2-acetate (IV; $n=4$)

This compound is prepared in the same manner as the preceding product. Yield of alpha isomer: 60.5%. M.P. 187°–188° C. (decomposition).

Analysis: C$_{22}$H$_{26}$N$_2$O$_6$S calculated: C 59.20%; H 5.83%; N 6.25%. found: C 59.15%; H 5.90%; N 6.25%.

| NMR spectrum (in DMSO—DSS): | | |
|---|---|---|
| 1.35 ppm | singlet | 9H (tert-butyl) |
| 1.62 ppm | singlet | 6H (cyclopentyl) |
| 2.1 ppm | singlet | 2H (cyclopentyl) |
| 2.73 ppm | singlet | 1H (H$_4$) |
| 4.95 ppm | quartet | 2H (H$_2$ and H alpha to ester) |
| 8.0 ppm | singlet | 4H (aromatic) |

I.R. spectrum (KBr): 3305 cm$^{-1}$ (NH); 1763 cm$^{-1}$ (CO phthalimido); 1735 cm$^{-1}$ (CO ester).

1704 cm$^{-1}$ (CO acid); 762 cm$^{-1}$ (ortho-disubstituted phenyl).

1.3. Tert-butyl-8-carboxy-alpha-phthalimido-5-thia-7-azaspiro[3.4]octane-6-acetate (IV, $n=4$)

This compound is prepared as described in paragraph 1.1. above. Yield of alpha isomer: 10%. M.P. 156°–157° C.

| NMR spectrum (in CDCl$_3$—TMS): | | |
|---|---|---|
| 1 to 3 ppm | multiplet | 6H (cyclobutyl) |
| 1.45 ppm | singlet | 9H (tert-butyl) |
| 3.82 ppm | singlet | 1H (H$_8$) |
| 5.05 ppm | quartet | 2H (H$_6$ and H alpha to butylester) |
| 7.5 and 8.7 ppm | multiplet | 5H (pyridine: impurity or salt) |
| 7.3 ppm | singlet | 4H (phthalimido) |

I.R. spectrum (KBr): 3330 cm$^{-1}$ (NH); 1769 cm$^{-1}$ (CO of the phthalimido group); 1725 cm$^{-1}$ (CO tert-butyl ester); 1705 cm$^{-1}$ (CO carboxyl); 708 cm$^{-1}$ (ortho-disubstituted phenyl).

1.4. Tert-butyl 4-carboxy-alpha-phthalimido-1-thia-3-azaspiro[4.6]undecane-2-acetate is prepared in the same manner 2.1. Tert-butyl 4-benzyloxycarbonyl-alpha-phthalimido-1-thia-3-azaspiro[4.5]decane-2-acetate (V; n=5).

8.5 g. (0.05 mole) of benzyl bromide are first added all at once and then 3.43 g. (0.034 mole) of triethylamine are added to a solution of 12 g. (0.026 mole) of tert-butyl-4-carboxy-alphaphthalimido-1-thia-3-azaspiro[4.5]decane-2-acetate in 130 ml. of anhydrous dimethylformamide. The reaction mixture is left to stand overnight at ambient temperature and then it is poured on to ice and 10 ml. of 6N hydrochloric acid are added followed by extraction with benzene. The organic phase is first washed with a 5% aqueous solution of sodium hydrogen carbonate and then with water, dried over anhydrous sodium sulfate, filtered and finally evaporated to dryness. After recrystallization from a mixture of diethyl ether and hexane (50/50), 12 g. (0.0215 mole) of tert-butyl 4-benzyloxycarbonyl-alpha-phthalimido-1-thia-3-azaspiro[4.5]decane-2-acetate are obtained. Yield: 82.7%. M.P. 165°–166° C.

Analysis: C$_{30}$H$_{34}$N$_2$O$_6$S calculated: C 65.45%; H 6.19%; N 5.09%. found: C 65.25%; H 6.25%; N 5.08%.

| NMR spectrum (in CDCl$_3$—TMS): | | |
|---|---|---|
| 1.45 ppm | singlet | 9H (tert-butyl) |
| 1 to 2 ppm | multiplet | 10H (cyclohexyl) |
| 2.7 ppm | multiplet | 1H (H$_3$) |
| 3.72 ppm | singlet | 1H (H$_4$) |
| 5.0 ppm | quartet | 2H (H$_2$ and H alpha to the butyl ester) |
| 5.15 ppm | quartet | 2H (CH$_2$ benzyl) |
| 7.35 ppm | singlet | 5H (phenyl of the benzyl group) |
| 7.80 ppm | multiplet | 4H (phenyl of the phthalimido group) |

I.R. spectrum (KBr): 3342 cm$^{-1}$ (NH); 1768 cm$^{-1}$ (CO of the phthalimido group); 1725 and 1710 cm$^{-1}$ (CO of esters); 753 cm$^{-1}$ (ortho-disubstituted phenyl); 706 and 695 cm$^{-1}$ (mono-substituted phenyl).

Mass spectrum: m/e 550 (M$^{+\cdot}$), 535, 516, 491, 476, 449, 290 (100%).

2.2. Tert-butyl 4-benzyloxycarbonyl-alpha-phthalimido-1-thia-3-azaspiro[4.4]nonane-2-acetate (V; n=4)

This compound is prepared in the same manner as the preceding compound. Yield: 78.4%.

Analysis: C$_{29}$H$_{32}$N$_2$O$_6$S calculated: C 64.93%; H 5.97%; N 5.22%. found: C 65.00%; H 5.52%; N 5.80%.

| NMR spectrum (CDCl$_3$—TMS): | | |
|---|---|---|
| 1.4 ppm | singlet | 9H (tert-butyl) |
| 1.3 to 3 ppm | multiplet | 8H (cyclopentyl) |
| 4.0 ppm | singlet | 1H (H$_4$) |
| 5.1 ppm | quartet | 2H (H$_2$ and H alpha to the tert-butyl ester) |
| 7.3 ppm | singlet | 5H (phenyl of the benzyl group) |
| 7.8 ppm | multiplet | 4H (phenyl of the phthalimido group) |

I.R. spectrum (KBr): 3335 cm$^{-1}$ (NH); 1770 cm$^{-1}$ (CO of the phthalimido group); 1725 and 1705 cm$^{-1}$ (CO of the esters); 762 cm$^{-1}$ (ortho-disubstituted phenyl); 747 and 692 cm$^{-1}$ (mono-substituted phenyl).

Mass spectrum: m/e 536 (M$^{+\cdot}$), 521,479,435,276 (100%).

2.3. Tert-butyl 8-benzyloxycarbonyl-alpha-phthalimido-5-thia-7-azaspiro[3.4]octane-6-acetate (V; n=3).

This compound is prepared in the same manner. Yield: 82%.

Analysis: C$_{28}$H$_{30}$N$_2$O$_6$S calculated: C 63.04%; H 5.80%; N 5.07%. found: C 63.22%; H 5.83%; N 5.00%.

2.4. Tert-butyl 4-benzyloxycarbonyl-alpha-phthalimido-1-thia-3-azaspiro[4.6]undecane-2-acetate is prepared in the same manner

III. Preparation of tert-butyl alpha-amino-thia-azaspiroalkaneacetates and the corresponding alpha-amino-thia-azaspiroalkaneacetic acids 1.1. Tert-butyl alpha-amino-4-benzyloxycarbonyl-1-thia-3-azaspiro[4.5]decane-2-acetate (VI; n=5).

71 ml. of a solution of anhydrous dimethylformamide containing 2 moles per liter of hydrazine hydrate (i.e. 0.142 mole) are added dropwise over a period of about 30 minutes at 0° C. to a suspension of 70.5 g. (0.128 mole) of tert-butyl 4-benzyloxycarbonyl-alphaphthalimido-1-thia-3-azaspiro[4.5]decane-2-acetate in 150 ml. anhydrous dimethylformamide. The reaction mixture is allowed to warm up to ambient temperature, with magnetic stirring, and to the resulting clear solution are added 120 ml. of 1.203N hydrochloric acid over a period of 1.5 hours. A precipitate of phthalohydrazide is formed, which is filtered off and washed several times with water, whereupon the mother liquors are evaporated in vacuo (bath temperature: maximum 40° C.) and the residue is taken up in a mixture of acetone and diethyl ether. There are finally obtained 43.2 g. (yield 73.7%) of tert-butyl alpha-amino-4-benzyloxycarbonyl-1-thia-3-azaspiro[4.5]decane-2-acetate hydrochloride.

M.P. 175°–176° C. (decomposition).

Analysis: C$_{22}$H$_{32}$N$_2$O$_4$S.HCl calculated: C 57.8%; H 7.22%; N 6.13%. found: C 58.5%; H 7.64%; N 6.81%.

| NMR spectrum (in DMSO—DSS): | | |
|---|---|---|
| 1.45 ppm | singlet | 9H (tert-butyl) |
| 1 to 2 ppm | multiplet | 10H (cyclohexyl) |
| 4 to 5 ppm | multiplet | 2H (H$_2$ and H alpha to the butyl ester) |
| 5.25 ppm | singlet | 2H (CH$_2$ benzyl) |
| 7.43 ppm | singlet | 5H (phenyl) |
| 8.55 ppm | multiplet | 3H (—NH$_2$ . HCl) |

I.R. spectrum (KBr): 3340 cm$^{-1}$ (NH); 1790 and 1710 cm$^{-1}$ (CO esters); 736 and 688 cm$^{-1}$ (mono-substituted phenyl).

Mass spectrum: m/e 421 (M+• + H•), 420, 319 and 290 (100%).

1.2. Tert-butyl alpha-amino-4-benzyloxycarbonyl-1-thia-3-azaspiro[4.4]nonane-2-acetate (VI; n=4).

This compound is prepared in the same manner as the preceding compound. Yield: 86.5%. M.P. 157°-158° C. Analysis: not significant, because it is a mixture of mono- and dihydrochlorides.

| NMR spectrum (in DMSO—DSS): | | |
|---|---|---|
| 1.45 ppm | singlet | 9H (tert-butyl) |
| 1.58 ppm | multiplet | 6H (cyclopentyl) |
| 2.05 ppm | multiplet | 2H (cyclopentyl) |
| 2.75 ppm | singlet | ½ H (mono- and |
| 2.90 ppm | singlet | ½ H  dihydrochlorides) |
| 4.0 ppm | multiplet | 2H (H₂ and H alpha to the butyl ester) |
| 5.23 ppm | singlet | 2H (CH₂ benzyl) |
| 7.42 ppm | singlet | 5H (phenyl) |
| 8.25 ppm | multiplet | 3H (—NH₂ . HCl) |

I.R. spectrum (KBr): 3330 cm⁻¹ (NH); 1723 and 1708 cm⁻¹ (CO esters); 740 and 682 cm⁻¹ (mono-substituted phenyl).

Mass spectrum: m/e 407 (M+• + H•), 406 (M+•), 350 and 276 (100%).

1.3. Tert-butyl alpha-amino-8-benzyloxycarbonyl-5-thia-7-azaspiro[3.4]octane-6-acetate (VI; n=3).

20.8 g. (0.04 mole) of tert-butyl 8-benzyloxycarbonyl-alphaphthalimido-5-thia-7-azaspiro[3.4]octane-6-acetate are suspended in 30 ml. of anhydrous dimethylformamide. 22 ml. of a freshly prepared solution containing 2 moles of hydrazine hydrate per liter of dimethylformamide are added to this suspension, at 0° C, while stirring, in an atmosphere of nitrogen and over a period of about 30 minutes.

The product dissolves, and the solution is allowed to warm up to 10° C over a period of 30 minutes. 93 ml of an 0,98N aqueous solution of hydrochloric acid are then added over a period of 15 minutes. After 2 hours stirring, the medium cristallizes in bulk. It is diluted with 10 ml of water and the precipitate is filtered off. This precipitate is then triturated with chloroform and this organic phase is evaporated off after drying over sodium sulfate. There are thus obtained 9.8 g. of tert-butyl alpha-amino-8-benzyloxycarbonyl-5-thia-7-azaspiro[3.4]octane-6-acetate. Yield: 57,3%. M.P. 160°-161° C (decomposition).

Analysis: C₂₀H₂₈N₂O₄S.HCl calculated: C 56.01%; H 6.76%; N 6.53%. found: C 55.99%; H 6.60%; N 6.51%.

I.R. spectrum (KBr): 3330 cm⁻¹ (NH) 1725 cm⁻¹ (C=O benzyl ester) 1713 cm⁻¹ (C=O tert-butyl ester) 745 and 692 cm⁻¹ (mono-substituted phenyl)

1.4. Tert-butyl alpha-amino-4-benzyloxycarbonyl-1-thia-3-azaspiro[4.6]undecane-2-acetate is prepared in the same manner 2.1. Alpha-amino-4-benzyloxycarbonyl-1-thia-3-azaspiro[4.5]decane-2-acetic acid (VII; n=5).

Dry gaseous hydrogen chloride is introduced rapidly for 1.25 hours at a temperature between 0° and 5° C., into a suspension of 4.1 g. (0.009 mole) of tert-butyl alpha-amino-4-benzyloxycarbonyl-1-thia-3-azaspiro[4.5]decane-2-acetate in 60 ml. of anhydrous nitromethane. Dissolution is practically complete. The remaining insoluble material is filtered off, the filtrate is subjected to a vacuum of 40 mm. Hg. in order to eliminate excess gaseous hydrogen chloride and then 200 ml. of diethyl ether are added. The reaction mixture is kept in a refrigerator for 2 hours and the resulting precipitate is then filtered off and washed several times with diethyl ether. There are finally obtained 3.5 g. (yield 92%) of alpha-amino-4-benzyloxycarbonyl-1-thia-3-azaspiro[4.5]decane-2-acetic acid in the form of a mixture of mono- and dihydrochlorides. M.P. 132°-135° C. (decomposition).

Analysis: calculated for Cl⁻ (dihydrochloride) 16.24%; found 14.60%.

| NMR spectrum (in trifluoroacetic acid (TFA—TMS)): | | |
|---|---|---|
| 1 to 2.5 ppm | multiplet | 10 to 11H (cyclohexyl) |
| 4.8 ppm | singlet | 1H (H₄) |
| 5.45 ppm | quartet | 2H (CH₂ benzyl) |
| 5.5 to 6.1 ppm | multiplet | 2H (H₂ and H alpha to the COOH) |
| 7.5 ppm | singlet | 5H (phenyl) |
| ±10 ppm | multiplet | 3H (—NH₂ . HCl) |

Mass spectrum: no molecular ion (M=364), but m/e 320 (M+• − CO₂), 319 (M+• − COOH), 290, etc.

2.2. Alpha-amino-4-benzyloxycarbonyl-1-thia-3-azaspiro[4.4]nonane-2-acetic acid (VII; n=4).

This compound is prepared in the same manner as the preceding compound, in a yield of 66%. It is also obtained in the form of a mixture of mono- and dihydrochlorides.

| NMR spectrum (in TFA—TMS): | | |
|---|---|---|
| 1.40 ppm | multiplet | 6H (cyclopentyl) |
| 1.80 ppm | multiplet | 2H (cyclopentyl) |
| 2.85 ppm | singlet | ½ H (H₄, mono- and |
| 2.95 ppm | singlet | ½ H  dihydrochlorides) |
| 4.4 to 5.8 ppm | multiplet | 4H (H₂ and H alpha to COOH and CH₂ benzyl) |
| 6.98 ppm | singlet | 5H (phenyl) |

Mass spectrum: no molecular ion, but m/e 306 (M+• − CO₂), 305 (M+• − COOH) and 276

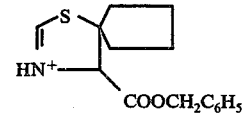

2.3. Alpha-amino-8-benzyloxycarbonyl-5-thia-7-azaspiro[3.4]octane-6-acetic acid (VII; n=3).

This compound is prepared in the same manner as the preceding compound. Yield: 95%. M.P. 89°-91° C (decomposition).

Analysis: C₁₆H₂₀N₂O₄S.HCl calculated: C 51.61%; H 5.64%; N 7.52%; found: C 50.12%; H 5.56%; N 7.30%.

I.R. spectrum: 3400 cm⁻¹ (ammonium); 1728 cm⁻¹ (C=O ester and acid); 745 and 690 cm⁻¹ (mono-substituted phenyl).

2.4. Alpha-amino-benzyloxycarbonyl-1-thia-3-azaspiro[4.6]undecane-2-acetic acid is prepared in the same manner.

IV. Preparation of benzyl 6'-tritylamino-spiro[cycloalkane-1,2'-penam]-3'-carboxylates.

1. Benzyl 6'-tritylamino-spiro[cyclopentane-1,2'-penam]-3'-carboxylate (IX; n=4).

To a solution of 33 g. (0.085 mole) of alpha-amino-benzyloxycarbonyl-1-thia-3-azaspiro[4.4]nonane-acetic acid in 600 ml. of dichloromethane, there are added at about −20° C. first and all at once 80 g. (0.288 mole) of trityl chloride and then slowly and still at the same temperature, 79 g. (0.78 mole) of triethylamine in 100 ml. of dichloromethane. The reaction mixture is stirred for one hour at a temperature between −20° and −10° C. and then left to stand overnight in a refrigerator. The reaction mixture is then poured on to ice and water, acidified to pH 6 with dilute phosphoric acid and decanted and the aqueous phase is extracted with chloroform. The organic phases are combined, washed with water, dried over anhydrous sodium sulfate and evaporated to dryness. There are thus obtained 110 g. of crude product which is suspended in 750 ml. of anhydrous nitromethane. Cooling is effected with an ice-bath and, over a period of one hour, there is added a solution of 50 g. (0.4 mole) of N,N'-diisopropylcarbodiimide (DCI) in 100 ml. of nitromethane. The reaction mixture is allowed to warm up to ambient temperature and stirring is continued overnight. The precipitate formed (19.6 g.; M.P. 153°–154° C.) is filtered off and the filtrate is evaporated to dryness (maximum bath temperature 30° C.). The residue is subjected to chromatography on silica (eluent: chloroform). There are thus obtained 27.5 g. of benzyl 6'-tritylamino-spiro[cyclopentane-1,2'-penam]-3'-carboxylate. Yield: 56.5%. M.P. 143°–144° C. (from benzene-hexane).

| NMR spectrum (in CDCl$_3$—TMS): | | |
|---|---|---|
| 1.80 ppm | multiplet | 8H (cyclopentyl) |
| 2.90 ppm | singlet | 1H (H$_3$') |
| 4.50 ppm | multiplet | 2H (H$_5$' and H$_6$') |
| 5.10 ppm | singlet | 2H (CH$_2$ benzyl) |
| 7.30 ppm | multiplet | (tritol impurity) |
| 1.15 ppm | doublet | (DCI impurity) |

I.R. spectrum (KBr): 1765 cm$^{-1}$ (CO beta-lactam); 1745 cm$^{-1}$ (CO ester).

Mass spectrum: m/e 574 (M$^{+\bullet}$), 497 (M$^{+\bullet}$ − phenyl), 331.

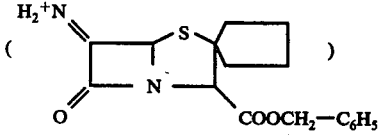

2. Benzyl 6'-tritylamino-spiro[cyclohexane-1,2'-penam]-3'-carboxylate (IX; $n=5$).

This compound is obtained in the same manner as the preceding compound in a yield of 80%. M.P. 157°–158° C. (from toluene)

Analysis: C$_{37}$H$_{36}$N$_2$O$_3$S calculated: C 75.51%; H 6.18%; N 4.76%. found: C 75.47%; H 6.20%; N 4.73%.

I.R. spectrum (KBr): 1775 cm$^{-1}$ (CO beta-lactam) 1733 cm$^{-1}$ (CO ester)

Mass spectrum: m/e 588 (M$^{+\bullet}$; 7.5%), 345 (M$^{+\bullet}$ −(C$_6$H$_5$)$_3$C; 36%), 290

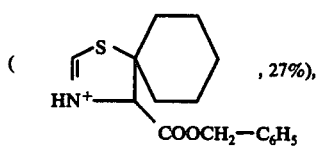

243 (C$_6$H$_5$)$_3$C$^+$; 100%).

3. Benzyl 6'-tritylamino-spiro[cyclobutane-1,2'-penam]-3'-carboxylate. (IX; $n=3$) This compound is prepared in the same manner as the preceding compound. However, it is obtained in the form of an amorphous, non crystallizable product, the I.R. spectrum of which shows the presence of a beta-lactam by a typical band at 1770 cm$^{-1}$. This product is used as such for the following stage.

4. Benzyl 6'-tritylamino-spiro[cycloheptane-1,2'-penam]-3'-carboxylate is prepared similarly.

V. preparation of benzyl 6'-amino-spiro[cycloalkane-1,2'-penam[-3'-carboxylate p-toluenesulfonates.

1. Benzyl 6'-amino-spiro[cyclohexane-1,2'-penam]-3'-carboxylate p-toluenesulfonate (X; $n=5$).

To a magnetically stirred solution of 31.4 g. (0.0534 mole) of benzyl 6'-tritylamino-spiro[cyclohexane-1,2'-penam]-3'-carboxylate in 300 ml. of anhydrous acetone, there is added a solution of 10.2 g. (0.0535 mole) of p-toluene-sulfonic acid monohydrate in 300 ml. of anhydrous acetone. After stirring for 2.5 hours at ambient temperature, a precipitate is obtained which is removed by filtration, washed with acetone and then with diethyl ether and dried. 10.1 g. of benzyl 6'-amino-spiro[cyclohexane-1,2'-penam]-3'-carboxylate p-toluenesulfonate are obtained. Yield: 36.5%.

M.P. 163°–164° C.

Analysis: C$_{18}$H$_{22}$N$_2$SO$_3$.p-TS calculated: C 57.91%; H 5.79%; N 5.40%. found: C 58.00%; H 5.83%; N 5.36%.

I.R. spectrum (KBr): 1784 cm$^{-1}$ (CO beta-lactam); 1735 cm$^{-1}$ (CO ester).

Mass spectrum: m/e 347 (M$^{+\bullet}$ + H$^{\bullet}$), 290, 200, 183, 165.

2. Benzyl 6'-amino-spiro[cyclopentane-1,2'-penam]-3'-carboxylate p-toluenesulfonate (X; $n=4$).

This compound is prepared in the same manner as the preceding compound. Yield: 46.5%.

Analysis: C$_{17}$H$_{20}$N$_2$SO$_3$.p-TS calculated: C 57.74%; H 5.56%; N 5.56%. found: C 57.80%; H 5.58%; N 5.58%.

| NMR spectrum (DMSO—TMS): | | |
|---|---|---|
| 1.5 to 2.2 ppm | multiplet | 8H (cyclopentyl) |
| 2.3 ppm | singlet | 3H (CH$_3$ of p—TS acid) |
| 4.8 ppm | singlet | 1H (H$_3$') |
| 5.25 ppm | singlet | 2H (CH$_2$ benzyl) |
| 5.35 ppm | 2 doublets | (J=4.6 cycles per second) 2H (H$_5$' and H$_6$') |
| 7.40 ppm | singlet | 5H (phenyl) |
| 7.35 ppm | quartet | 4H (aromatic H of p—TS acid) |

I.R. spectrum (KBr): 1788 cm$^{-1}$ (CO beta-lactam); 1730 cm$^{-1}$ (CO ester).

Mass spectrum: m/e 332 (M$^{+\bullet}$), and 276

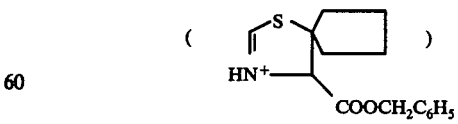

3. Benzyl 6'-amino-spiro[cyclobutane-1,2'-penam]-3'-carboxylate p-toluene-sulfonate (X; $n=3$).

1.3 g (0.0023 mole) benzyl 6'-tritylamino-spiro[cyclobutane-1,2'-penam]-3'-carboxylate are dissolved in 25 ml of anhydrous acetone. 0.447 g (0.0023 mole) of p-toluenesulfonic acid monohydrate dissolved in 5 ml acetone are added thereto. The reaction mixture is stirred at ambient temperature for 2 hours, then the p-toluenesulfonate is precipitated by the addition of 150 ml of anhydrous diethyl ether. 520 mg. (0.001 mole) of benzyl 6'-amino-spiro[cyclobutane-1,2'-penam]-3-carboxylate p-toluenesulfonate are thus recovered. Yield: 46.8%. M.P. 144°-5° C (decomposition).

Analysis: $C_{16}H_{18}N_2SO_3 \cdot p\text{-TS}$ calculated: C 56.33%; H 5.31%; N 5.71%. found: 58.05%; H 5.39%; N 5.90%.

I.R. spectrum (KBr): 3430 cm$^{-1}$ ($-NH_3^+$) 1775 cm$^{-1}$ (C=O beta-lactam) 1727 cm$^{-1}$ (C=O benzyl ester) 792 cm$^{-1}$ (1,4-disubstituted phenyl) 737 and 680 cm$^{-1}$ (mono-substituted phenyl)

| NMR (DMSO—TMS): | | |
|---|---|---|
| 1.5 to 2.5 ppm | multiplet | 6H (cyclobutyl) |
| 2.3 ppm | singlet | 3H (CH$_3$ of p—TS acid) |
| 5.15 ppm | doublet | 1H (H$_{5'}$) |
| 5.17 ppm | singlet | 1H (H$_{3'}$) |
| 5.25 ppm | singlet | 2H (CH$_2$ benzyl) |
| 5.45 ppm | doublet | 1H (H$_{6'}$) |
| 7.3 ppm | quartet | 4H (aromatic of p—TS acid) |
| 7.42 ppm | singlet | 5H (phenyl) |

Mass spectrum: m/e 318 (molecular ion), 262

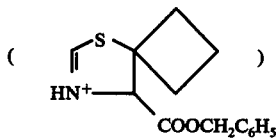

4. Benzyl 6'-amino-spiro[cycloheptane-1,2'-penam]-3'-carboxylate p-toluene-sulfonate is prepared similarly.

VI.

6'-Amino-spiro[cycloalkane-1,2'-penam]-3'-carboxylic acids.

1. 6'-Amino-spiro[cyclohexane-1,2'-penam]-3'-carboxylic acid (I; n=5)

To a suspension of 5.8 g. (0.011 mole) of benzyl 6'-amino-spiro[cyclohexane-1,2'-penam]-3'-carboxylate p-toluenesulfonate in 100 ml. of dichloromethane, there is added a solution of 1.3 g. (0.012 mole) of triethylamine in 10 ml. of dichloromethane. The compound dissolves instantaneously. The reaction mixture is washed with water and the solvent is evaporated off after drying over anhydrous sodium sulfate. The residue is taken up in a minimum amount (about 20 ml.) of ethyl acetate, and 100 ml. of water and 13.2 ml. (0.012 mole) of 1.154 N hydrochloric acid are added. The aqueous phase is decanted off, 3 g. of palladium on carbon (10% Pd) catalyst are added and hydrogenolysis is carried out at a pressure of about 2 atmospheres for 2 hours. The solution is then filtered through Hyflo-cel, adjusted to a pH of 4 with ammonium hydroxide and lyophilized. There are thus obtained 2.8 g. of product which is taken up in a minimum of water, filtered and washed with acetone and then with diethyl ether. There is finally obtained 1.9 g. (0.0074 mole) of 6'-amino-spiro[cyclohexane-1,2'-penam]-3'-carboxylic acid. Yield: 67.5%. M.P. 208°-210° C. (decomposition).

Analysis: $C_{11}H_{16}N_2O_3S$ calculated: C 51.56%; H 6.25%; N 10.94%. found: C 50.10%; H 6.45%; N 9.60%.

| NMR spectrum (in DMSO—TMS): | | |
|---|---|---|
| 1.70 ppm | multiplet | 10H (cyclohexyl) |
| 4.25 ppm | singlet | 1H (H$_{3'}$) |
| 4.55 ppm | doublet | (J=4.5 cycles per second) 1H (H$_{5'}$) |
| 5.35 ppm | doublet | (J=4.5 cycles per second) 1H (H$_{6'}$) |

I.R. spectrum (KBr): 3155 cm$^{-1}$ (NH$_3^+$); 1785 cm$^{-1}$ (CO beta-lactam); 1605 cm$^{-1}$ (CO acid).

2. The following compounds are prepared in the same manner:
6'-amino-spiro[cyclobutane-1,2'-penam]-3'-carboxylic acid;
6'-amino-spiro[cyclopentane-1,2'-penam]-3'-carboxylic acid;
6'-amino-spiro[cycloheptane-1,2'-penam]-3'-carboxylic acid.

We claim:

1. A 6'-amino-spiro[cycloalkane-1,2'-penam]-3'-carboxylic acid, a salt or an ester thereof, of the formula

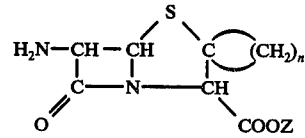

wherein Z is a hydrogen or an alkali metal atom, or a group protecting the carboxylic function, and n is a whole number of from 3 to 6.

2. A compound as claimed in claim 1, wherein Z is a benzyl radical.

3. A compound as claimed in claim 1, namely 6'-amino-spiro[cyclobutane-1,2'-penam]-3'-carboxylic acid.

4. A compound as claimed in claim 1, namely 6'-amino-spiro[cyclopentane-1,2'-penam]-3'-carboxylic acid.

5. A compound as claimed in claim 1, namely 6'-amino-spiro[cyclohexane-1,2'-penam]-3'-carboxylic acid.

6. A compound as claimed in claim 1, namely 6'-amino-spiro[cycloheptane-1,2'-penam]-3'-carboxylic acid.

* * * * *